US008200506B2

(12) United States Patent
Kil

(10) Patent No.: US 8,200,506 B2
(45) Date of Patent: Jun. 12, 2012

(54) INTEGRATED HEALTH MANAGEMENT PLATFORM

(75) Inventor: David H. Kil, Santa Clara, CA (US)

(73) Assignee: Accenture Global Services Limited, Dublin (IE)

( * ) Notice: Subject to any disclaimer, the term of this patent is extended or adjusted under 35 U.S.C. 154(b) by 1207 days.

(21) Appl. No.: 11/612,763

(22) Filed: Dec. 19, 2006

(65) Prior Publication Data

US 2008/0147438 A1     Jun. 19, 2008

(51) Int. Cl.
*G06Q 50/00* (2012.01)
(52) U.S. Cl. .................... 705/3; 705/2; 707/737
(58) Field of Classification Search .............. 705/2–3; 707/373–740
See application file for complete search history.

(56) References Cited

U.S. PATENT DOCUMENTS

| 5,813,863 | A | 9/1998 | Sloane et al. | |
|---|---|---|---|---|
| 5,879,163 | A | 3/1999 | Brown et al. | |
| 5,893,072 | A | 4/1999 | Zizzamia | |
| 6,039,688 | A | 3/2000 | Douglas et al. | |
| 6,317,700 | B1 | 11/2001 | Bagne | |
| 6,523,009 | B1 * | 2/2003 | Wilkins | 705/3 |
| 6,560,541 | B1 * | 5/2003 | Singh | 702/19 |
| 6,561,811 | B2 | 5/2003 | Rapoza et al. | |
| 6,684,208 | B2 | 1/2004 | Kil | |
| 6,769,915 | B2 | 8/2004 | Murgia et al. | |
| 6,817,979 | B2 | 11/2004 | Nihtila | |
| 7,091,976 | B1 | 8/2006 | Ostermann et al. | |
| 7,128,577 | B2 | 10/2006 | Renaud | |
| 7,379,066 | B1 | 5/2008 | Ostermann et al. | |
| 7,609,270 | B2 | 10/2009 | Ostermann et al. | |
| 8,033,996 | B2 | 10/2011 | Behar | |
| 2002/0002474 | A1 * | 1/2002 | Michelson et al. | 705/3 |
| 2002/0147617 | A1 | 10/2002 | Schoenbaum et al. | |
| 2002/0156654 | A1 * | 10/2002 | Roe et al. | 705/3 |

(Continued)

FOREIGN PATENT DOCUMENTS

EP           1 936 525 A1    6/2008

OTHER PUBLICATIONS

Chang, John T. et al. "Patient's Global Ratings of Their Health Care Are Not Associated with the Technical Quality of Their Care," Annals of Internal Medicine, May 2, 2006, pp. 665-672, W149-W157, vol. 144, No. 9, American College of Physicians, USA.

(Continued)

*Primary Examiner* — Gerald J. O'Connor
*Assistant Examiner* — Sind Phongsvirajati
(74) *Attorney, Agent, or Firm* — Fish & Richardson P.C.

(57) ABSTRACT

Apparatuses, computer media, and methods for supporting health needs of a consumer by processing input data. An integrated health management platform supports the management of healthcare by obtaining multi-dimensional input data for a consumer, determining a health-trajectory predictor from the multi-dimensional input data, identifying a target of opportunity for the consumer in accordance with the health-trajectory predictor, and offering the target of opportunity for the consumer. Multi-dimensional input data may include claim data, consumer behavior marketing data, self-reported data, and biometric data. A consumer may be assigned to a cluster based on the multi-dimensional input data and a characteristic of the consumer may be inferred. A cluster may be associated with a disease progression, and a target of opportunity is determined from the cluster and the disease progression. An impact of the target of opportunity may be assessed by delivering treatment to a consumer at an appropriate time.

24 Claims, 8 Drawing Sheets

U.S. PATENT DOCUMENTS

| | | | |
|---|---|---|---|
| 2003/0065535 A1* | 4/2003 | Karlov et al. ............... | 705/2 |
| 2003/0126101 A1 | 7/2003 | Rao et al. | |
| 2003/0130873 A1* | 7/2003 | Nevin et al. ............... | 705/3 |
| 2003/0206170 A1 | 11/2003 | Bickmore et al. | |
| 2003/0212579 A1 | 11/2003 | Brown et al. | |
| 2004/0002634 A1 | 1/2004 | Nihtila | |
| 2005/0021750 A1 | 1/2005 | Abrams | |
| 2005/0027544 A1 | 2/2005 | Newstead et al. | |
| 2005/0101845 A1 | 5/2005 | Nihtila | |
| 2005/0137015 A1 | 6/2005 | Rogers et al. | |
| 2005/0182659 A1* | 8/2005 | Huttin ............... | 705/2 |
| 2005/0206610 A1 | 9/2005 | Cordelli | |
| 2005/0216529 A1 | 9/2005 | Ashtekar et al. | |
| 2005/0235062 A1 | 10/2005 | Lunt et al. | |
| 2005/0288910 A1 | 12/2005 | Schlessinger et al. | |
| 2006/0089543 A1 | 4/2006 | Kim et al. | |
| 2006/0105825 A1 | 5/2006 | Findlay | |
| 2006/0143569 A1 | 6/2006 | Kinsella et al. | |
| 2006/0210045 A1 | 9/2006 | Valliath et al. | |
| 2006/0256132 A1 | 11/2006 | Shin et al. | |
| 2007/0050715 A1 | 3/2007 | Behar | |
| 2008/0147440 A1 | 6/2008 | Kil | |
| 2008/0147441 A1 | 6/2008 | Kil | |
| 2008/0201442 A1 | 8/2008 | Ostermann et al. | |
| 2010/0042697 A1 | 2/2010 | Ostermann et al. | |

OTHER PUBLICATIONS

Galvin, Robert, "Pay-for-Performance: Too Much of a Good Thing? A Conversation with Martin Roland," Health Affairs, Sep. 6, 2006, pp. w412-w419, Project HOPE—The People-to-People Health Foundation, Inc., USA.

Cumming, Robert B. et al. "A Comparative Analysis of Claims-Based Methods of Health Risk Assessment for Commercial Populations," May 24, 2002, pp. 1-85, USA.

Keckley, Paul H. "Evidence-based Medicine and Managed Care: Applications, Challenges, Opportunities," Vanderbilt Center for Evidence-based Medicine, Dec. 2003, pp. 1-61, USA.

Pope, Gregory C. "Diagnostic Cost Group Hierarchical Condition Category Models for Medicare Risk Adjustment," Health Care Financing Administration, Dec. 21, 2000, pp. 1-293, USA.

Cohen, A.M. "Reducing Workload in Systematic Review Preparation Using Automated Citation Classification," Journal of the American Medical Informatics Association, Mar./Apr. 2006, pp. 206-219, USA.

Lin, Jimmy et al. "'Bag of Words' is not enough for Strength of Evidence Classification", In the Proceeding of the 2005 Annual Symposium of the American Medical Informatics Association, Oct. 2005, 1 page, USA.

Ruggenenti, Piero et al. "Preventing Microalbuminuria in Type 2 Diabetes," The New England Journal of Medicine, Nov. 4, 2004, pp. 1941-1951, vol. 351, No. 19, Massachusetts, USA.

Wilcox, Adam et al. "Medical Text Representations for Inductive Learning," Department of Medical Informatics, 2000, pp. 1-5, AMIA, USA.

WILLEMSSEN, Joel C. "Weakness in Managing Information Technology Hinder Fight Against Fraud and Abuse," Medicare Automated Systems, pp. 1-7, United States General Accounting Office, USA.

Agrawal, Vishal et al. "Consumer-Directed Health Plan Report-Early Evidence is Promising" Jun. 2005, pp. 1-18, McKinsey & Company, USA.

McNeill, Dwight, "Do Consumer-Directed Health Benefits Favor the Young and Healthy?" Health Affairs, Jan./Feb. 2004, pp. 186-193, vol. 23, No. 1, Project Hope, USA.

Kil, David et al. "Propensity Score Primer with Extensions to PCA-based Score Shaping and Dynamic Impact Analysis," DMAA Conference, Apr. 16, 2004, pp. 1-15, USA.

Gilmer, T. et al. "The Medicare Rx Model: Pharmacy-Based Risk Adjustment for Public Programs," Med Care, 2001, pp. 1188-1202, vol. 39, No. 11, USA.

Wynia, M.K. et al. "Physician Manipulation of Reimbursement Rules for Patients," JAMA, Apr. 12, 2000, pp. 1858-1865, vol. 283, No. 14, USA.

Kil, David et al. "Pattern Recognition and Prediction with Applications to Signal Characterization" 1996, pp. 111-154, Springer-Verlag, USA.

Parente, S. et al. "Evaluation of the Effect of a Consumer-Driven Health Plan on Medical Care Expenditure and Utilization," Health Services Research, Aug. 2004, pp. 2, vol. 39, issue 4, USA.

Kil, David et al. "Pattern Recognition and Prediction with Applications to Signal Characterization" 1996, pp. 333-346, Springer-Verlag, USA.

Ahn, Hyungil, et al. "Affective Cognitive Learning and Decision Making: The Role of Emotions," The 18th European Meeting on Cybernetics and Systems Research (EMCSR 2006), Apr. 18-19, 2006, Vienna, Austria, pp. 1-6.

Clark, et al. "A Simple Statistical Method for Measuring how Life Events Affect Happiness", International Journal of Epidemiology, vol. 31, 2002, pp. 1139-1146.

Eddy, et al. "Clinical Outcomes and Cost-Effectiveness of Strategies for Managing People at High Risk for Diabetes", Annals of Internal Medicine, vol. 143, No. 4, Aug. 16, 2005, pp. 251-264 and W-53-W-68 (30 pages).

Eddy, et al. "Validation of the Archimedes Diabetes Model", Diabetes Care, vol. 26, No. 11, Nov. 2003, pp. 3102-3110.

Ellin, "Who's Older, You or Your Body? Tests Suggest Answers", New York Times, Sep. 28, 2006, 3 pages.

Giles, Jim. "Concept of 'personal space' survives in virtual reality," Sep. 11, 2006, pp. 1-3, Linden Research, Inc. USA.

Kahneman "Experience Utility and Objective Happiness: A Moment-Based Approach", Choices, Values and Frames, Chapter 37, Cambridge University Press, 2000, 26 pages.

Kent, S.L. "Making an MMOG for the Massses," GameSpy, Oct. 10, 2003, pp. 1-11, USA.

Kleinfield, "Living at an Epicenter of Diabetes, Defiance and Despair", New York Times, Jan. 10, 2006, 7 pages.

Kleinfeld "Modern Ways Open India's Doors to Diabetes", New York Times, Sep. 13, 2006, 9 pages.

Konomi, et al. "Supporting Colocated Interactions Using RFID and Social Network Displays", IEEE Pervasive Computing, vol. 5, No. 3, Jul.-Sep. 2006, pp. 48-56.

Lake, The Relationship Between Poor Health Behavior and Medicare Costs, Honors Thesis, Stanford University, May 10, 2005, downloaded from the internet at: http://economies.stanford.edu/files/Theses/Theses_2005/Lake.pdf on Feb. 24, 2012, 53 pages.

Morgensen, "Whispers of Mergers Set off Bouts of Suspicious Trading", New York Times, Aug. 27, 2006, 7 pages.

Novak, et al. "Measuring Consumer Experience in Online Environments: A Structural Modeling Appoach", Marketing Science, vol. 19, No. 1, Winter, 2000 pp. 22-42.

Nissen, et al. "Effect of Muraglitazar on Death and Major Adverse Cardiovascular Events in Patients with Type 2 Diabetes Mellitus", Journal of the American Medical Association, vol. 294, Oct. 20, 2005, 6 pages.

Robinson, et al. "Simulation, Scenarios, and Emotional Appraisal: Testing the Convergence of Real and Imagined Reactions to Emotional Stimuli", Personality and Social Psychology Bulletin, vol. 27, No. 11, Nov. 2001 pp. 1520-1532.

Roizen, Michael F., Real Age Are You as Young as You can Be?, 1999, entire book, Cliff Street Books, New York, USA.

Schiesel, S. "Online Game, Made in U.S., Seizes the Globe," The New York Times, Sep. 5, 2006, pp. 1-5, USA.

Schlessinger, Leonard, et al. "Archimedes: a new model for simulating health care systems—the mathematical formulation," Journal of Biomedical Informatics, 2002, pp. 37-50, Elsevier Science, USA.

Storz, et al. "Lessons from the e-Campus Display Deployments", IEEE Pervasive Computing, vol. 5, No. 3, Jul.-Sep. 2006, pp. 40-47.

Tsai, et al. "Systematic Review: Evaluation of Major Commercial Weight Loss Programs in the United States" Annals of Internal Medicine, vol. 142, No. 1, Jan. 4, 2005, pp. 56-66.

Wilson, et al. "Affective Forecasting" Advances in Experimental Social Psychology, vol. 35, 2003, pp. 345-411.

Yee, Nicholas "The Psychology of MMORPGs: Emotional Investment, Motivations, Relationship Formation, and Problematic Usage," Avatars at Work and Play: collaboration and Interaction in Shared Virtual Environments, Mar. 2006, pp. 1-31, Springer-Verlag, London, UK.

Zhou, et al. "A Computer Simulation Model of Diabetes Progression, Quality of Life, and Cost", Diabetes Care, vol. 28, No. 12, Dec. 2005 pp. 2856-2863.

* cited by examiner

INTEGRATED HEALTH MANAGEMENT PLATFORM

FIELD OF THE INVENTION

This invention relates generally to healthcare management. More particularly, the invention provides apparatuses, computer media, and methods for supporting health needs of a consumer by processing input data.

BACKGROUND OF THE INVENTION

The U.S. healthcare industry is a $2T economy with the rate of growth far exceeding that of general inflation. With the aging global population, the current healthcare crisis is expected to worsen, threatening the health of global economy. The existing healthcare ecosystem is zero-sum. The recent pay-for-performance (P4P) experiment by the National Health Services in the United Kingdom resulted in mixed outcomes with incentive-based payments far exceeding the budget with uncertain improvements in patient health. On the other hand, a recent study on the sophistication of healthcare consumers reveals that there is little correlation between consumers' perception of care and the actual quality of healthcare delivered as measured by RAND's 236 quality indicators. Furthermore, given the high churn rate and the propensity of employers to seek the lowest-cost health plan, payers are motivated to focus primarily on reducing short-term cost and carving out the cream-of-the-crop population, resulting in perverse benefit design.

In healthcare, predictive models are used to improve underwriting accuracies and to identify at-risk members for clinical programs, such as various condition-centric disease management programs. Unfortunately, predictive models typically use year-1 payer claims data to predict year-2 cost. Some predictive modeling vendors predict future inpatient or emergency-room episodes since they represent high-cost events. The emphasis on cost makes sense given that the impetus for predictive models came from private and government payers struggling with rising healthcare costs.

Evidence-based medicine (EBM) is an attempt to apply scientific evidence to making care decisions for patients. A lot of EBM guidelines are derived from medical journals, where teams of researchers rely on randomized controlled trials and observational studies to draw inferences on the efficacy of various treatments on carefully selected patient populations. Pharmacovigilance or study of adverse drug reactions is an example of EBM.

Current EBM vendors, such as Active Health Management, a wholly owned subsidiary of Aetna, and Resolution Health, rely on a team of physicians reading and codifying relevant medical journals. The resulting EBM database is applied to population claims data consisting of medical, Rx, and lab claims data in order to identify patients not receiving proper EBM guidelines, i.e., with "gaps" in treatment. Physicians of the identified patients are contacted through faxes or telephone calls with instructions or recommendations on how to close the gaps in treatment. A number of shortcomings exist with the current EBM implementation. Many EBM studies suffer from small sample size, thus making generalization difficult and sometimes inaccurate. A corollary of the first shortcoming is that most EBM studies are at a selected population level and do not provide drilldown information at a sub-population level. That is, if not everyone benefits from an EBM guideline, it may be dangerous to apply the guideline to the entire study population, which begs for a careful tradeoff between specificity and sensitivity. Guidelines typically do a poor job of translating study outcomes into metrics that end stakeholders care about. For example, payers pay a particular attention to cost, which is not the same as improving surrogate endpoints that are therapeutic in nature with various time frames for healing or outcomes improvement. Publication bias and conflicting results encourage ad hoc decision making on the part of payers in the area of utilization management, such as coverage denials and medical necessity reviews. Furthermore, relying on published guidelines discourages the use of autonomous or loosely guided search for anomalies or precursors to adverse outcomes using a large of amount of integrated data assets and intelligent search algorithms based on machine learning.

Clearly, there is a desperate need for an integrated solution for providing healthcare management.

BRIEF SUMMARY OF THE INVENTION

The present invention provides apparatuses, computer media, and methods for supporting health needs of a consumer by processing input data.

With one aspect of the invention, an integrated health management platform supports the management of healthcare by obtaining multi-dimensional input data for a consumer, determining a health-trajectory predictor from the multi-dimensional input data, identifying a target of opportunity for the consumer in accordance with the health-trajectory predictor, and offering the target of opportunity for the consumer. Multi-dimensional input data may include claim data, consumer behavior marketing data, self-reported data, and biometric data.

With another aspect of the invention a consumer is assigned to a cluster or clusters based on the multi-dimensional input data. A characteristic of the consumer may be inferred from a subset of the multi-dimensional input data.

With another aspect of the invention, a cluster is associated with a disease progression, where the cluster is associated with at least one attribute of a consumer. A target of opportunity is determined from the cluster and the disease progression. An impact of the target of opportunity may be assessed by delivering treatment to a consumer at an appropriate time.

With another aspect of the invention, a target of opportunity is extracted from medical information using a set of rules for the multi-dimensional input data.

With another aspect of the invention, a previous event that occurred before a subsequent transition event is identified. A correlation between the previous event and the subsequent transition event is measured from historical data to assign multidimensional strength or utility indicators to a discovered rule.

With another aspect of the invention, an enrollment healthcare selection for the consumer is recommended based on multi-dimensional input data.

BRIEF DESCRIPTION OF THE DRAWINGS

The present invention is illustrated by way of example and not limited in the accompanying figures in which like reference numerals indicate similar elements and in which.

DETAILED DESCRIPTION OF THE INVENTION

Figure 1:
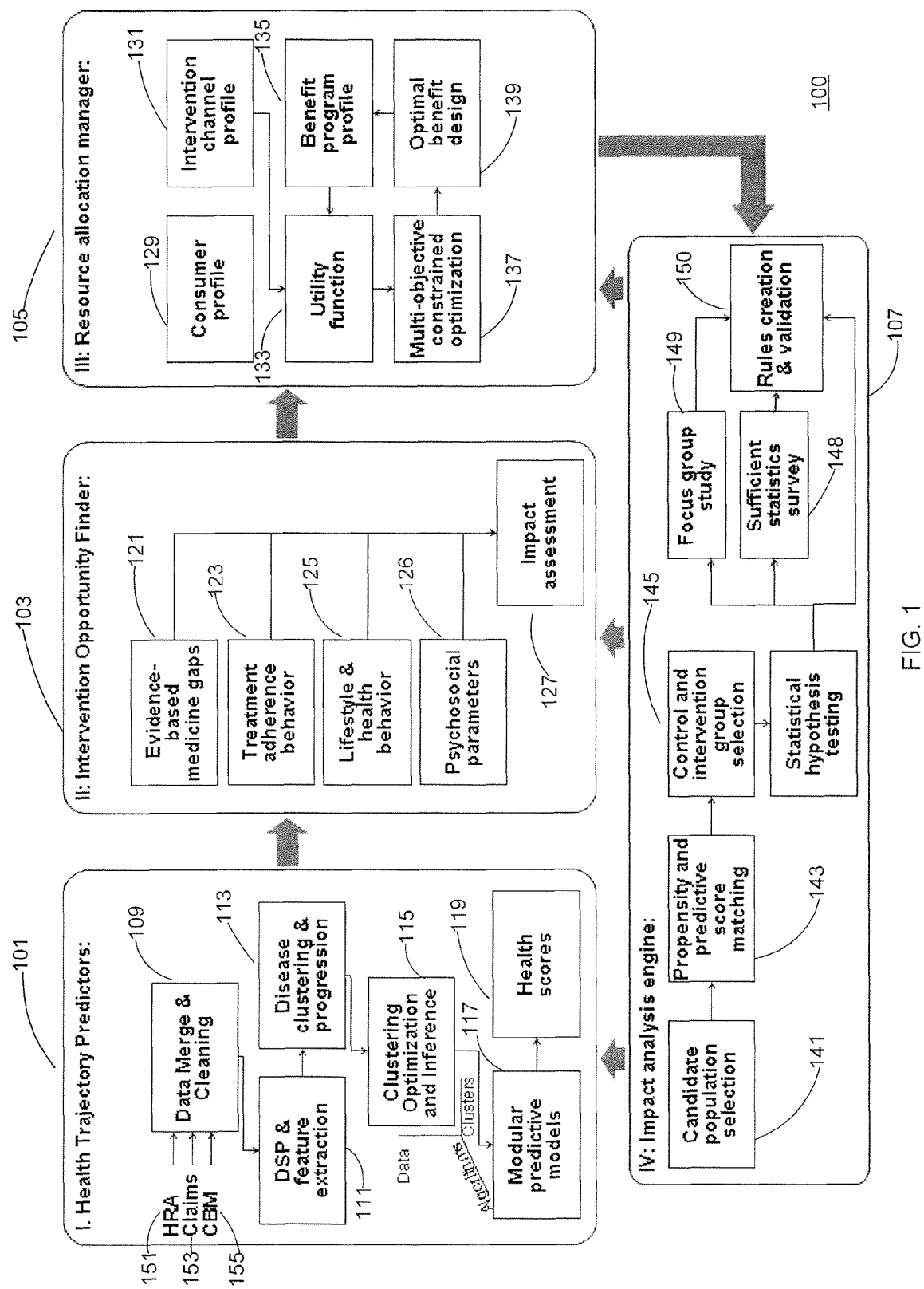
FIG. 1 shows an architecture of an integrated health management (IHM) platform in accordance with an embodiment of the invention.

Integrated Health Management Platform in a Service Oriented Architecture (SOA) Framework FIG. 1 shows an architecture of integrated health management (IHM) platform 100 in accordance with an embodiment of the invention. IHM platform 100 creates for payers a virtuous circle of integrated informatics leading to improved and real-time decision making leading to healthier members leading to improved profitability and cost savings leading to improved market share. For consumers who must share an increasing burden of medical costs, the execution of IHM platform may lead to improved health and subsequent cost savings. In the following discussion, a consumer may be an employee of a company or an individual choosing a healthcare plan from a plurality of plans and consuming products/services from various healthcare stakeholders. An objective of the consumer is to maximize benefits associated with good health by choosing a healthcare plan that is "best" for the individual or his/her family and improving health through timely preventive and proactive health actions.

The IHM platform consists of the following four components:

1. Multimode health-trajectory predictors module 101: Instead of focusing on predicting future cost alone using claims data as most predictive models do now, multimode health-trajectory predictors leverage claims data 153, self-reported data 151, and consumer behavior marketing data 155, coupled with inference engines 115, to provide a comprehensive set of future attributes useful to assess the level of impact through various consumer-engagement channels. Claims data 153 may include medical claims, pharmacy claims, prior authorization, and lab results (e.g., blood tests) for a consumer. Consumer-engagement channels may encompass secure e-mails, Interactive Voice Recording (IVR) calls, cellphone text messages, and nurse calls. Data Merge & Cleaning 109 performs extract-transform-load (ETL) of disparate data assets to form a consumer-centric view while cleaning data prior to weak-signal transformation through digital signal processing (DSP) and feature extraction 111. Disease clustering and progression module 113 subsequently forms disease clusters and estimates disease progression probabilities. Clustering optimization & inference 115 performs clustering using attributes that are meaningful from the perspective of predicting future health trajectories and impactability with the inference engine filling in unobserved variables using the instantiated variables. A modular predictive model is developed for each consumer cluster so that a collection of locally optimized predictive models can provide a globally optimal performance 117. Finally, a set of health scores encompassing health scores, behavior/lifestyle scores, engagement scores, impact scores, data-conflict scores, cost scores, and clinical scores is output 119.

2. Targets-of-opportunity finder 103: Leveraging consumer-understanding technologies, an evidence-based-medicine (EBM) supercharger (shown as EBM supercharger 300 in FIG. 3), and an autonomous insight crawler, one can identify targets of opportunities in various consumer touch points. The four major opportunities lie in clinical gaps 121, treatment adherence 123, lifestyle/behavior 125, and psychosocial parameters 126. Impact assessment is made based on the aggregate future impact of all the identified targets of opportunities 127.

3. Resource-allocation manager 105: Resource-allocation manager (RAM) 105 funnels the right members to the right consumer touch points at the right time by maximizing multi-objective functions. Also included in RAM 105 are consumer-understanding technologies and iterative benefit design borrowing salient concepts from adaptive conjoint analysis, predictive modeling, and Pareto multi-objective optimization. Furthermore, mixing-in currently available technologies into consumer touch points in conjunction with dynamic progressive content tailoring allows one to go beyond the typical nurse-based care model, which is inherently not scalable especially with the projected worsening nurse shortage in the labor market. (Resource-allocation manager 105 is Pareto efficient if no consumer can be made better off without another consumer being made worse off.) The fundamental idea here is building a multi-objective constrained optimization engine 137 as a function of consumer, intervention-channel, benefit-program profiles (129, 131, 135) and utility functions 133 derived from the impact analysis engine.

4. Impact-analysis engine 107: This module tells one what works for which population segments, by how much, and why in a drilldown mode. It facilitates the use of utility functions in the framework of resource-allocation optimization as done in defense battlefield resource management. The methodology employed uses predictive modeling, combinatorial and stochastic feature optimization with respect to outcomes, and propensity-score shaping. After selecting candidate population for analysis 141, one performs thorough matching in the two-dimensional space of propensity and predictive scores 143 to create control and intervention groups 145 for an "apple-to-apple comparison." One then create rules of engagement for statistically significant outcomes, which are further validated through focus-group study 149 and survey using the minimum number of necessary questions 148. Validated rules 150 are stored in the master rules database for production implementation.

The four above components 101-107 complement one another and are ideally suited to assessing the incremental benefits of bringing new data assets and business processes into enterprise operations. In order to facilitate integration into and compatibility with typical payer enterprise applications, the IHM implementation (e.g., IMH platform 100) adheres to an enhanced Service Oriented Architecture (SOA) framework. A key idea here is maximizing synergy among business process primitives, data models, and algorithm models so that one can reduce latency between the generation of actionable knowledge and its production implementation.

Figure 1A:
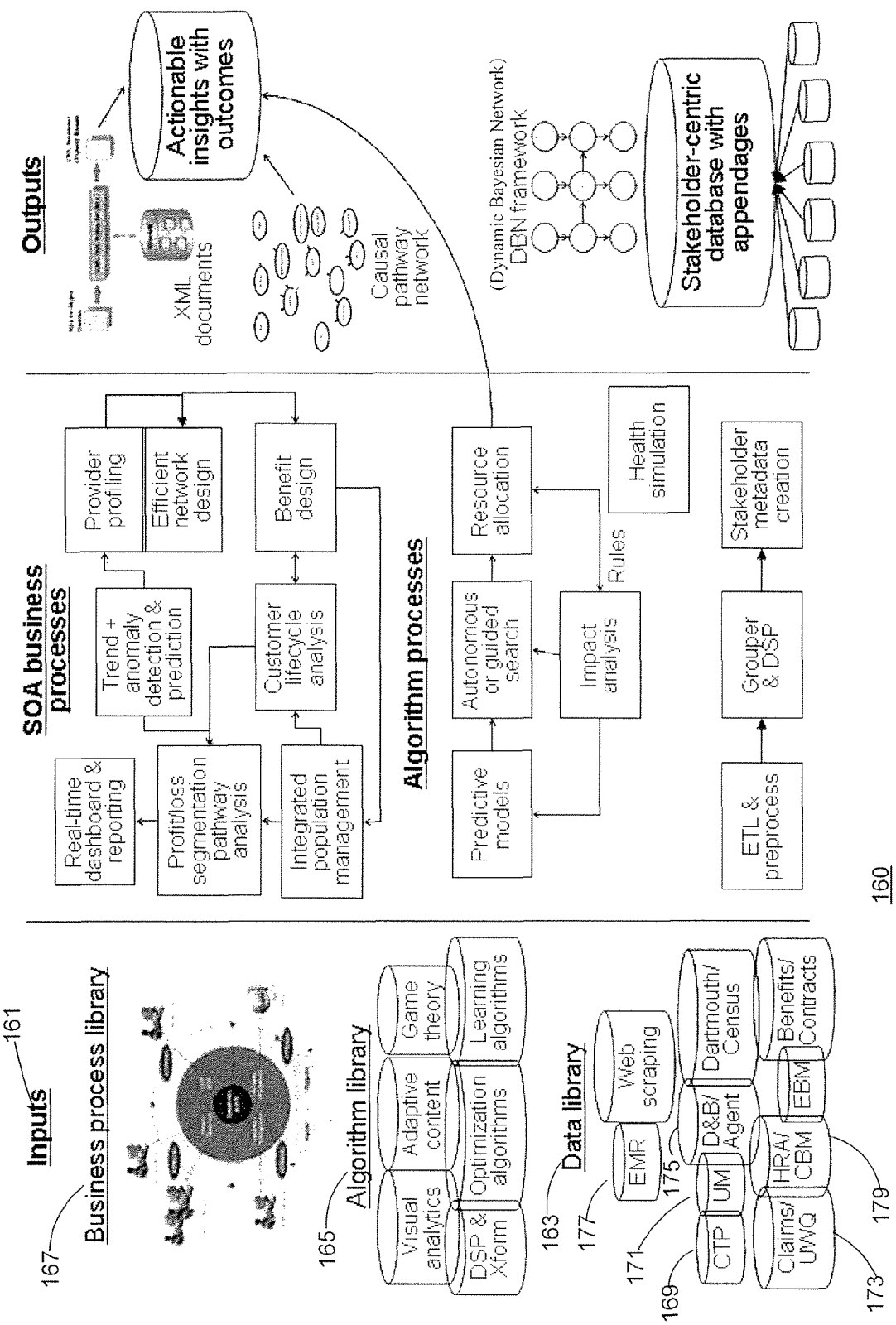
FIG. 1A shows a Service Oriented Architecture (SOA) framework in accordance with an embodiment of the invention.

FIG. 1A shows Service Oriented Architecture (SOA) framework 160 of IHM platform 100 in accordance with an embodiment of the invention. Framework 160 increases synergy in data models, mathematical models, and business-process models that are important in ensuring the success of IHM Platform 100. Inputs 161 consist of data library 163, algorithm library 165, and business-process libraries 167, which get updated with the latest discoveries. The processing layer uses the building blocks of business processes and algorithms tailored to underlying data models to produce intermediate processing outputs as well as actionable insights that feed to multimedia outputs for dissemination to the key stakeholders.

Data library 163 includes Consumer Touch Points (CTP) 169, Utilization Management (UM) 171, Underwriting Questionnaire (UWQ) 173, D&B: Dun & Bradstreet (D&B) database 175, Electronic Medical Records (EMR) 177, and Health Risk Assessment (HRA) database 179.

Multimode Health-Trajectory Predictors

Figure 2:
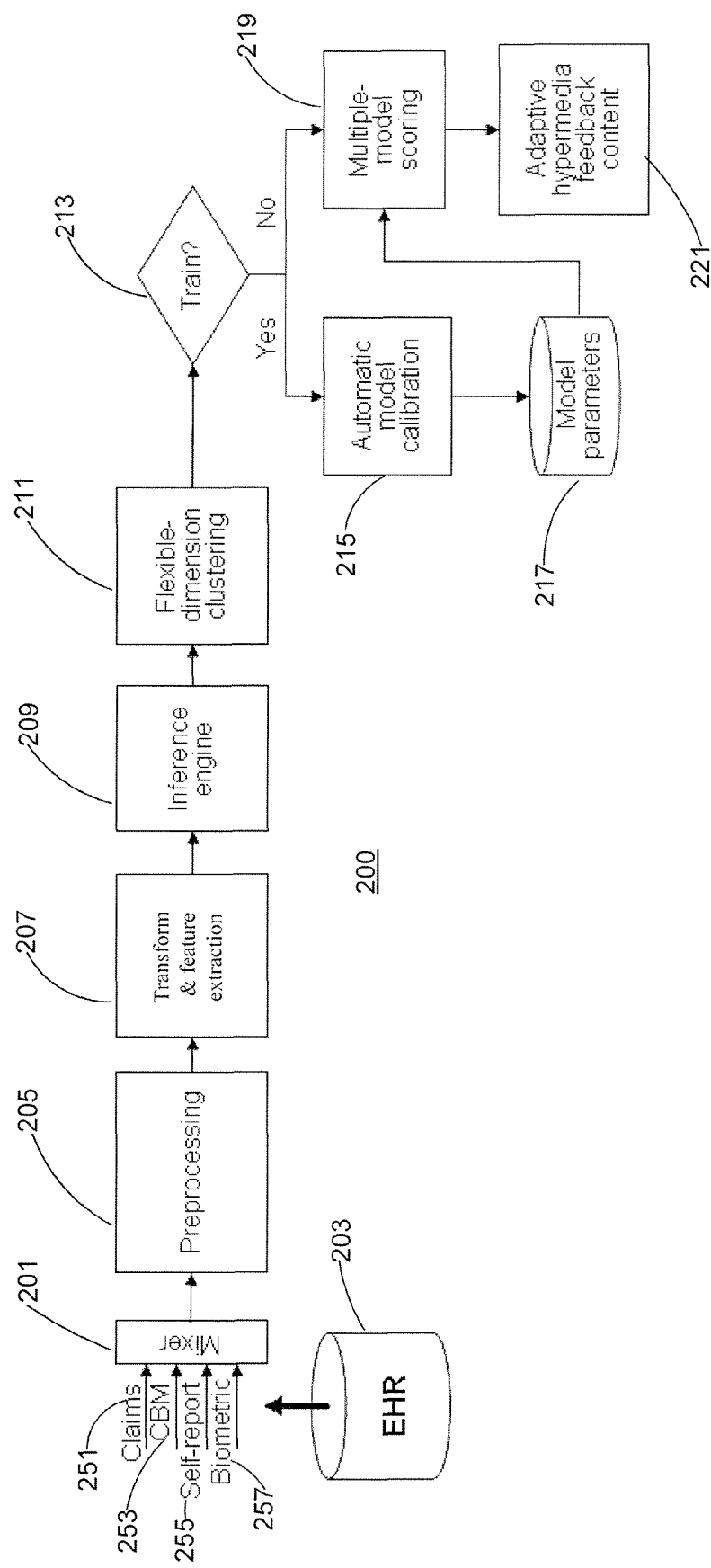
FIG. 2 shows a method of determining multimode health-trajectory predictors in accordance with an embodiment of the invention.

FIG. 2 shows process 200 for determining multimode health-trajectory predictors in accordance with an embodiment of the invention. Instead of focusing on cost prediction, multimode health-trajectory predictors attempt to understand current and predict transitions in Bayesian relationships among the many semi-orthogonal outcomes attributes so that one can maximize positive impact through delivering the right intervention touch points to the right consumers at the right time before adverse transitions occur.

In healthcare, predictive models are used to improve underwriting accuracies and to identify at-risk members for clinical programs, such as various condition-centric disease management programs. Typically, prior art predictive modes predict year-2 cost using year-1 payer claims data. Some prior art predictive modeling vendors predict future inpatient or emergency-room episodes since they represent high-cost events. The emphasis on cost makes sense given that the impetus for predictive models came from private and government payers struggling with rising healthcare costs.

Focusing on cost alone ignores the complex, multifaceted nature of healthcare consumers. Knowing future cost with R-sq of 10-25% is different from being able to impact the future health trajectory of each consumer. For example, it may be more beneficial to touch John suffering from pre-diabetic conditions with body mass index (BMI) of 32 than to intervene on behalf of Mark who has to go through kidney dialysis three times a week because of end-stage renal disease. From a cost perspective, Mark may be 20-40 times more expensive. But from an impact perspective, John would be a better candidate because his current conditions are more amenable to actions that can be taken now to prevent unpleasant consequences in the near future.

As a result of cost emphasis, prior art predictive models extract a standard set of features from Rx and/or medical claims data and apply linear regression or neural networks to predict year-2 cost. Typical features include disease flags and year-1 summary cost and utilization statistics, such as average inpatient cost per month, average Rx cost per month, # of physician visits per month, etc. Some predictive models divide the population into sub-groups using inputs from clinicians with the goal of designing a model tailored to each sub-group (MedAI). However, it may be quite difficult to design optimal clusters given the complexities of and interplays among the many factors that determine future health trajectories.

In order to address the shortcomings of the current generation of predictive models, an embodiment of the invention incorporates the following concepts:

1. Use of input data such as claims data 251, self-reported data 255, consumer behavior marketing (CBM) data 253, and biometric data 257 is augmented with inference engine 209 to predict multiple semi-orthogonal attributes with the goal of finding the best way to engage and motivate healthcare consumers to create positive impact. Input data is typically provided by electronic health record (EHR) database 203. Not everyone will have all the data assets. Therefore, key unknown variables need to be estimated using inference engine 209.

2. Flexible-dimension clustering process 211 creates an optimal set of consumer clusters from an impact perspective instead of using the same old disease hierarchy to create disease-centric consumer clusters.

3. Adaptive hypermedia content creation 221 leverages a comprehensive understanding of consumer needs and how to best provide a positive impact.

As shown in FIG. 2, inputs include:

Claims data 251: It is comprised of Rx/med/lab data, utilization-management (UM) data including pre-authorization, Rx/med benefit data, program touch-point data, Web log data, and limited member demographic data.

Consumer behavior marketing (CBM) data 253: This externally purchasable data provides inferred behavior, lifestyle, and attitudinal information on consumers from their demographic data and credit history.

Self-reported data 255: This includes health risk assessment (HRA), ecological momentary assessment (EMA), and experience sampling method (EMA) data administered through multiple communication channels, such as the Internet, cellphone, set top box, etc.

Biometric data 257: This encompasses data from wearable sensors (Bodymedia's BodyBugg™, Nike+ shoe sensor, polar band) and attachable sensors (glucometer, blood-pressure cuff, spirometer, etc.) transmitted through wired or wireless networks.

As shown in FIG. 2, processing includes:

Mixer 201: Not everyone will have all the data elements. Therefore, mixer 201 organizes incoming data into a schema appropriate for frame-based dynamical data processing. Furthermore, it differentiates between 0 and an empty set $\phi$.

Preprocessing 205: This step performs secondary data audit and consumer-centric data structure generation. Primary data audit occurs during data creation in enterprise data warehouse (EDW).

1) Data audit: Outliers are normalized using multi-pass peak-shearing. Multiple debit/credit entries and ghost claims are eliminated. It looks for potential gender/age mismatch errors (grandmother or father giving birth to a baby or a premature baby's neonatal claims being assigned to his or her parents) using a look-up table.

2) Consumer-centric data structure generation: For each consumer, we create an efficient data structure from memory and processing perspectives. It is a hierarchical structure encompassing the entire consumer touch-point suite of channels.

Transform 207: This step creates various bandpass-filtered maps over time. For instance, International Classification of Disease (ICD) 9/10 codes from medical claims and National Drug Codes (NDC) from Rx claims are converted into hierarchical condition-versus-time maps to facilitate the analysis of disease progression and the creation of disease clusters. Moreover, such a representation can help one to infer behavioral patterns from linking discrete events or following medication adherence for managing chronic conditions. A combination of ICD and Current Procedure Terminology (CPT) codes is used to derive Milliman & Robertson (M&R) categories over time, which is useful in assessing the utilization of various service types (inpatient, outpatient, emergency room, physician office visit, etc.) over time. Biometric data is processed through a large number of transformation algorithms, such as the fast Fourier transform, wavelet transform, local cosine transform, ensemble interval histogram, etc., in order to glean locally dynamic behaviors over time. Due to the infrequent nature of HRA and CBM data (i.e., people do not change their behavior or lifestyle every hour), locally dynamic behaviors serve as anchor points that vary much more slowly so that one can investigate the cumulative effects of linked local events over time on behavior change. The entire transformation process is analogous to multi-rate signal processing. At the end of transform, we extract a large number of static and dynamic features from each transformation space, as well as higher-order linked attributes spanning multiple transformation spaces in order to glean insights into disease clustering, disease progression, and their interplay with the consumer's psychosocial behavioral traits.

Inference engine 209: Knowing certain unobserved traits can be quite useful in devising tailored intervention strategies. Let $x_{claims}$, $x_{CBM}$, $x_{SR}$, and $x_{bio}$ represent the four data sets as previously discussed. If knowing one's body mass index (BMI) is desirable, one first builds modular predictive models from the sub-population that has BMI data such that $P(BMI|x_{claims})$, $P(BMI|x_{CBM})$, etc. constitute a feasible set of models for predicting BMI conditioned upon having other data assets. This model can be in the form of Bayesian networks, regression or classification algorithms leveraging parametric and non-parametric learning algorithms.

Flexible-dimension clustering 211: This is an iterative process leveraging multiple fitness functions and predictive models as part of clustering. This step generates a set of clusters for each outcomes variable such that the output dispersion compression is maximized for improved prediction accuracy.
1) For each outcomes variable, one performs feature optimization to find a sufficient-statistics feature subset.
2) One performs clustering using k-means, expectation-maximization (EM), and Kohonen's self-organizing feature map. After clustering, there are $N_C$ clusters for each outcomes variable. For each cluster, one calculates the dispersion $\sigma_i$, $i=1, \ldots, N_C$ of each of the outcomes distributions and compare it with the overall dispersion $\sigma_T$ from the entire population. The dispersion-compression ratio (DCR) $r_i = \sigma_T/\sigma_i > \gamma$, where $\gamma > 1$, is a predetermined dispersion-compression threshold for accepting the $i^{th}$ cluster based on its ability to compress the outcomes distribution. One creates a set of samples that pass the DCR test.
3) For the samples that do not pass the first DCR test, repeat steps 1-2 until there is no sample left or the number of remaining samples is less than the minimum sample size.

Automatic model calibration 215: In real-world problems, data characteristics remain rarely stationary over time. With process 200, step 213 determines whether training is needed to update process 200 for new medical developments. For example, introduction of new medical technologies and drugs, changes in benefit plans and fee-reimbursement schedules, changing demographics, and even macroeconomic cycles can affect data characteristics. Built-into the automatic model calibration algorithm 215 is a data-mismatch estimator that keeps track of statistical parameterization of key data assets over overlapping time frames and consumer clusters after removing secular trends, e.g., medical-cost inflation. Model parameters are updated and stored in model parameters database 217. During model initialization and subsequent re-calibration, the following takes place:
1) Perform preprocessing step 205, transform step 207, inferring step 209, and flexible dimension clustering step 211
2) Feature optimization for each consumer cluster and outcomes variable using combinatorial and stochastic algorithms
3) Model performance tuning to find the point of diminishing returns
4) Multiple-model combining Multiple-model scoring 219: Once process 200 has been trained, multiple-model scoring 219 is performed for input data 251-257. One generates the following health scores:
1) Health scores as a function of current chronic conditions and predicted disease progression
2) Behavior and lifestyle scores computed heuristically as a function of reported, observed (medication adherence, frequent ER visits, the level of interaction with care-management nurses, etc.), and inferred behavior and lifestyle attributes
3) Engagement scores as a function of reported, observed, and inferred psychosocial and collaborative-filtering parameters
4) Impact scores working in concert with evidence-based-medicine (EBM) supercharger 300 and utility functions associated with targets of opportunities and derived from the impact-analysis engine
5) Conflict scores as a function of discrepancies between reported and observed behavioral/lifestyle factors and claims data
6) Cost scores for multiple future time periods in chronic vs. acute categories
7) Clinical utilization scores in terms of inpatient, emergency room/urgent care centers, medication, etc.

Adaptive hypermedia content generation 221: This module generates a tailored report of 1-2 pages succinctly summarizing current health conditions, likely future states, targets of opportunities, action plan, and benefits with drilldown menu.

Figure 3:
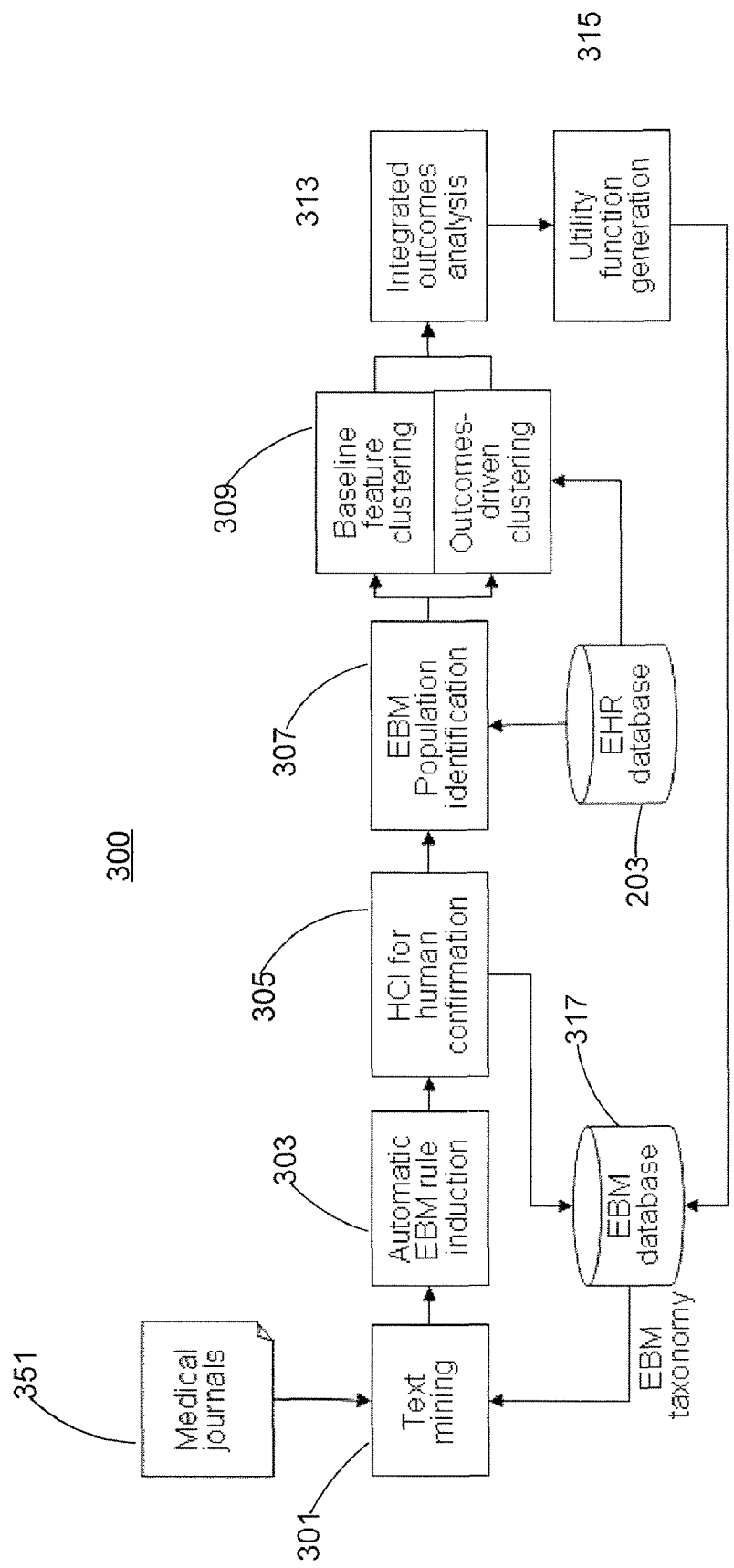
FIG. 3 shows a flow diagram for an evidence-based medicine supercharger in accordance with an embodiment of the invention.

In accordance with an embodiment of the invention, process 200 provides outputs including:
Consumer-centric metadata for a comprehensive view (both tabular and scientific visualization) of each consumer with appendages linking consumer-centric metadata to various stakeholders to facilitate stakeholder-centric data transformation
Health scores
Adaptive hypermedia content tailored to each consumer
Evidence-Based Medicine Supercharger
FIG. 3 shows a flow diagram for evidence-based medicine (EBM) supercharger 300 in accordance with an embodiment of the invention. From an EBM guideline or a medical journal article 351, evidence-based-medicine supercharger 300 generates a set of multidimensional inferred and observed utility functions, which is an essential ingredient in developing optimal resource allocation strategies. The utility function can be multidimensional at multiple levels of granularity in terms of patient or consumer clusters, leading to an M×N matrix, where M and N represent the number of utility components or objectives and the number of consumer clusters, respectively. For example, consumer clusters generated from the health-trajectory predictors may encompass the following groups: (1) those who are generally healthy from a claims perspective, but exhibit poor health habits in terms of high BMI and "couch-potato" characteristics; (2) those who suffer from chronic illnesses amenable from a lifestyle intervention, such as diabetes and cardiovascular disease; (3) people who have multiple co-morbid conditions, but one cannot find treatment-related claims records (N=3). From a segmented drilldown impact analyses of three intervention channels (Interactive Voice Response (IVR), health behavior coaching, and case management (M=3)), one determines that the most effective intervention channels for the three population clusters are (IVR, health behavior coaching), (health behavior coaching), (case management and health behavior coaching), respectively. The utility function is a 3×3 matrix, where each element $x_{ij}$ contains a utility score or return on investment for the $i^{th}$ intervention channel applied to the $j^{th}$ consumer cluster.

In accordance with an embodiment of the invention, evidence-based-medicine supercharger 300 includes:

Input Databases:

1) EBM database 317: It consists of EBM rules, taxonomy for inducing rule parameters from medical journal, population parameters, rule strength, mapping look-up tables that map condition and drug names to ICD-9 and NDC, respectively, and utility function. Population parameters encompass inclusion and exclusion criteria. Rule strength is a function of publication rank using a page-ranking algorithm, author prestige based on the number of connections in the publication network, journal prestige based on the number of circulation, sample size, percentage of total cost affected, longitudinal duration, and the number of corroborating articles. The EBM taxonomy facilitates efficient induction of EBM-rule parameters from an exemplary journal abstract as shown in the Appendix. More algorithmic details will be discussed in the processing-algorithm subsection.

2) Electronic Health Records (EHR) 203: This database contains claims data 251, self-reported data 255, and consumer behavior marketing (CBM) data 253.

Processing Algorithms

Text mining 301: The Appendix shows a semi-structured abstract from an article published in the New England Journal of Medicine. Instead of using a bag-of-words or natural-language-processing feature vector and a Naïve Bayes classifier to rank an abstract, one simply detects whether an abstract reports an outcomes study or not. This is a much easier problem and defers the strength-of-evidence classification until after integrated outcomes analysis. Next, one uses a combination of key words, tf*idf text weights (in which the importance of a word is based on its frequency of occurrence in a document and normalized by its natural frequency of occurrence in a corpus) with stemming and stop words, and distance measures from key words to fill in the hierarchical tree EBM database fields in the areas of:

1) Type of outcomes research
2) Patient characteristics: size, dropout rate (if available), characteristics in terms of inclusion and exclusion criteria, longitudinal duration, and trigger criteria
3) Reported results The distance measures are necessary to leverage lexical analysis to understand higher-level relations and concepts between words in a sentence or a paragraph.

Automatic EBM rule induction 303: Given the EBM database fields extracted from a medical journal, one uses secondary look-up tables to map drug names, diagnoses, and procedures onto NDC, ICD-9, CPT-4, and laboratory codes commonly used in claims-payment systems.

Human-Computer Interface (HCI) for human confirmation 305: The induced EBM rule along with the highlighted abstract is presented to a clinician for final confirmation with or without edit.

EBM population identification 307: One identifies potential control and intervention populations using the inclusion, exclusion, and trigger criteria. The presence or absence of the trigger criteria assigns a patient to the intervention or control group, respectively, provided that the patient satisfies the inclusion and exclusion criteria.

Dual-space clustering 309: This step creates meaningful consumer clusters that are homogeneous in the optimized baseline-period-attribute-and-outcomes (y) vector space. The baseline period equals the pre-intervention period of a fixed duration 1) For each EBM guideline, one builds models that predict various outcomes metrics. Associated with each predictive model is an optimal feature subset ($X \in R^N$, where N is the optimal feature dimension) derived from a combination of stochastic and combinatorial optimization algorithms.

2) In the vector space spanned by X, one performs clustering using k-means, expectation-maximization (EM), and Kohonen's self-organizing feature map algorithms. After clustering, there are Nc clusters. For each cluster, one calculates the dispersion $\sigma_i$, i=1, ..., $N_C$ of each of the outcomes distributions and compare it with the overall dispersion $\sigma_T$ from the entire population. The dispersion-compression ratio (DCR) $r_i = \sigma_T/\sigma_i > \gamma$, where $\gamma > 1$, is a predetermined dispersion-compression threshold for accepting the $i^{th}$ cluster based on its ability to compress the outcomes distribution for more precision in applying EBM from an outcomes perspective. One creates a set of accepted samples for which clusters in X are sufficiently precise for performing integrated outcomes analysis. One selects the clustering algorithm that provides the highest DCR.

3) For the remaining population samples, perform feature optimization to derive a new optimal feature subset $X^{(k)}$. Compress $X^{(k)}$ into $X_c$ ($\dim(X_c) \ll \dim(X^{(k)})$) using linear discriminant analysis (LDA) and discretized outcomes metrics should they be continuous. Next, perform clustering in the vector space spanned by $X_c$ and y. Prior to clustering, normalize the vector space so that mean and standard deviation of each component will be 0 and 1, respectively. The standard deviation of y can be higher to reflect its importance in determining clusters. Keep the clusters whose DCRs>1.

4) For the remaining clusters, repeat step iii until the number of remaining samples is below the minimum threshold, i.e., (k)→(k+1). The final remaining samples represent the final cluster.

Integrated outcomes analysis 313: For each cluster, perform case-controlled impact analysis leveraging predictive and propensity-score models to account for both regression to the mean and selection bias. A comprehensive set of outcomes metrics encompasses both observed and inferred variables. For the inferred variables, we estimate individual and cluster prediction accuracies so that we can assess the level of statistical significance as a function of cluster size and model accuracy.

Utility function generation 315: Finally we generate a set of utility functions.
1) Two-dimensional marginal utility functions over individual outcomes metrics and population clusters
2) One-dimensional utility function over a composite outcomes metric with weights
3) Pareto Frontier set for multiple outcomes metrics based on a user-defined multi-objective function Outputs of evidence-based-medicine supercharger 300 include:

Utility functions tailored to each stakeholder, a composite outcomes metric, or multi-objective optimization or Pareto-efficient plots Outcomes metrics

Autonomous Healthcare Data Exploration System

Figure 4:
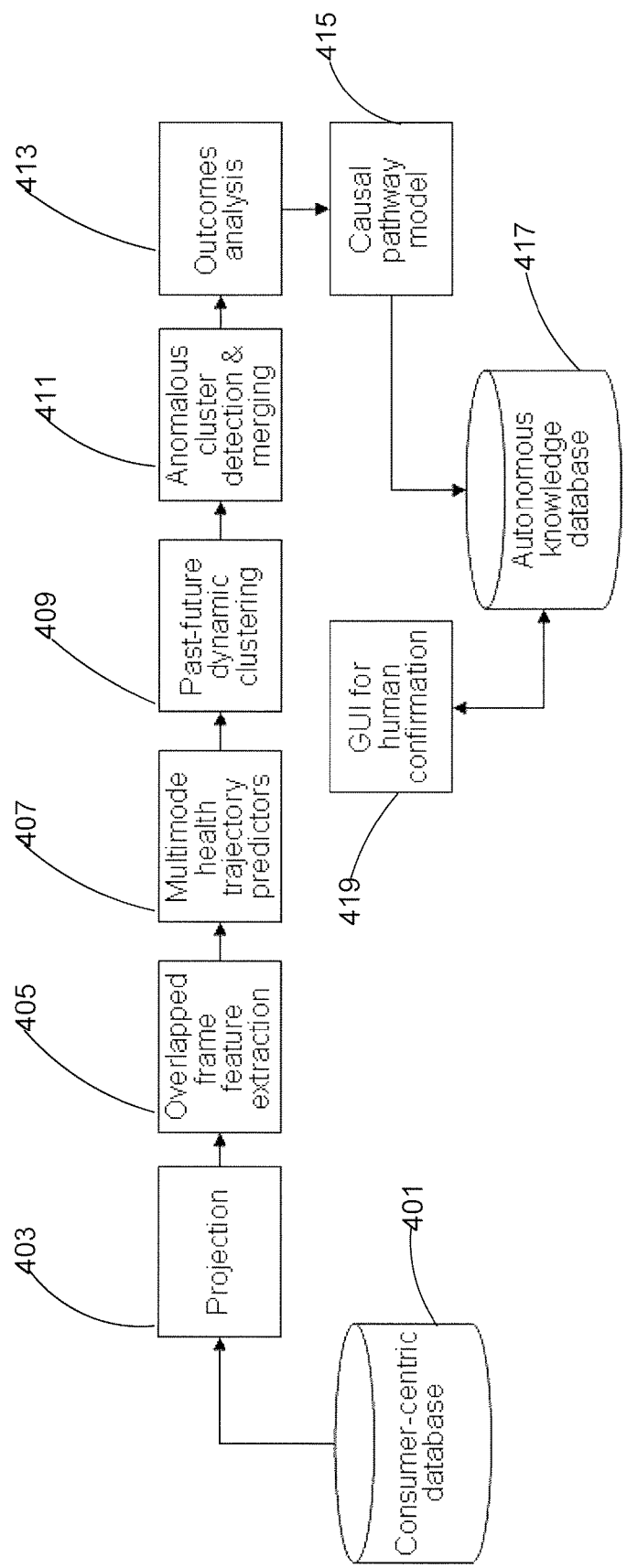
FIG. 4 shows a flowchart for an autonomous healthcare data exploration system in accordance with an embodiment of the invention.

FIG. 4 shows a flowchart for autonomous healthcare data exploration system 400 in accordance with an embodiment of the invention. Autonomous healthcare data exploration system 400 explores healthcare database to look for "interesting" relationships autonomously using various signal processing and data mining algorithms. There is often substantial hidden insight in healthcare data that can be discovered. Autonomous data exploration is sometimes associated with fraud detection. In healthcare, gaming or exploitation of loopholes in fee-reimbursement policies can be a serious problem, which has led to utilization management or medical necessity review by payers. For example, one study reports that 39% of physicians surveyed use at least one of the following three gaming methods:
1. Exaggerating the severity of patients' conditions
2. Changing patients' billing diagnoses
3. Reporting signs or symptoms that patients didn't have Fraud detection has been around for over two decades in a myriad of forms. It typically looks for outliers or uses models learned from labeled training data to identify suspicious activities for human confirmation. The two most widely used areas are in credit-card and financial industries. The U.S. Securities and Exchange Commission (SEC) and research boutique firms pore through tick-by-tick financial data to look for anomalous trading patterns that can signal insider trading.

Just to illustrate the difficulty of transitioning commercial antifraud solutions to healthcare, the U.S. Government Accountability Office reports that instead of adopting commercially available antifraud software to Medicare use, the Health Care Financing Administration (HCFA) chose to enter into a multi-year agreement with the Los Alamos National Laboratory, citing numerous difficulties with adopting commercial software. Unfortunately, no such software—commercial or custom-built—is in widespread use today.

The focus on fraud pits one stakeholder against another when outright fraud is relatively rare, and a soft form of exploiting system loopholes is more common in healthcare. Therefore, there is a need for a more sophisticated and less demeaning system focused on learning hidden causal relations between treatment and health outcomes (both positive and negative) so as to gain the widest possible acceptance from all the stakeholders.

FIG. 4 shows the flowchart of autonomous healthcare data exploration system 400, which leverages multimode health-trajectory predictors along with a consumer-centric database 401. Autonomous healthcare data exploration system 400 includes the following components:

Inputs
Consumer-centric database (CCDB) 401 consisting of membership, benefit-plan history, consumer-touchpoint history, claims, self-reported, consumer behavior marketing, provider, and evidence-based medicine data Autonomous knowledge database, which is empty in the beginning, but will be populated with new and iteratively refined knowledge Processing Projection 403: This step creates multiple projections of CCDB 401 over time so that one has a complete view of all that's happening to each consumer conditioned upon slowly-changing lifestyle, behavior, and psychographic parameters.

Overlapped frame feature extraction 405: From each time frame of each projection space, one extracts an appropriate number of summarization and dynamic features so that we can track their trajectories over time.

Multimode health-trajectory predictors 407: Predictors 407 predict future states of one's health around disease progression, engagement, and impact.

Past-future dynamic clustering 409: Clustering is performed on the vector space spanned by the current set of features and predicted attributes. In one embodiment of such a system, the current set of features encompasses the parameterization of current disease conditions, utilization of medical resources, and lifestyle/health behavior. Predicted attributes may include disease progression, the level of impactability, and future cost. The key idea is to cluster consumers based on both where they are today and where they are likely to transition to in the future.

Anomalous cluster detection and merging 411: Within each homogeneous cluster, one looks for outliers in joint and marginal spaces. Depending on the outlier-population size derived from each cluster, one merges outliers from multiple similar clusters to improve statistical power and significance.

Outcomes analysis 413: For each outlier cluster, one looks for attributes with commonality and differences between outliers and normal cases. This search for common and uncommon attributes facilitates case-controlled outcomes analysis with drilldown along with the understanding of factors responsible for differences in outcomes.

Causal pathway analysis 415: For each anomaly case identified, one uses a structural learning algorithm to induce a Bayesian network structure. Next, one ensures that causal parameters between control and test groups move in a logical way.

GUI for human confirmation 419: Each discovered knowledge is presented to a human expert for final confirmation and inclusion into the autonomous knowledge discovery database 417.

Outputs provided by autonomous healthcare data exploration system 400 include:
Extracted knowledge

Intelligent Health Benefit Design System

Figure 5:
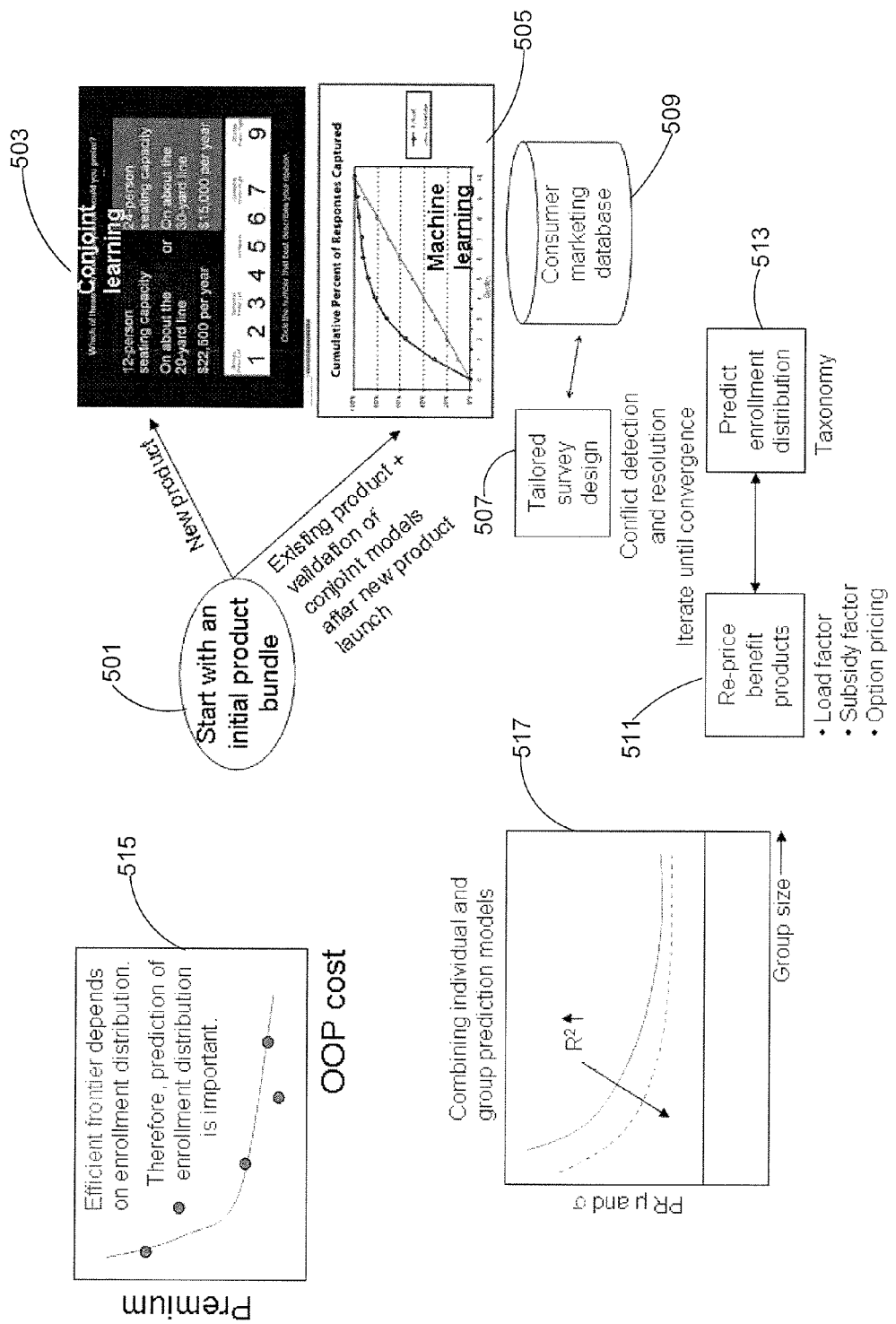
FIG. 5 shows an illustrative conceptual example of the optimal health benefit design in accordance with an embodiment of the invention.

FIG. 5 shows an illustrative conceptual example of the optimal health benefit design in accordance with an embodiment of the invention. An intelligent benefit design system leverages ideas from consumer-understanding technologies, predictive modeling, impact analysis, and multi-objective optimization to design an individually tailored benefit product that balances the conflicting needs of moral hazard and social insurance by finding the acceptable ratio of profitability to subsidization for each product or plan configuration in a product bundle.

Element 515 in FIG. 5 shows a simplified two-dimensional efficient frontier in the two-dimensional space of premium and out-of-pocket (OOP) cost with an indifference curve. That is, higher premiums are generally associated with lower OOP costs and vice versa. An insurance company starts out with an initial set of product bundles 501. If the company introduces a new product for which no prior enrollment data is available, then the product enrollment distribution is estimated using adaptive conjoint learning and prediction 503. On the other hand, if product changes are evolutionary, then one can use prior enrollment data to develop and deploy predictive models to estimate the new product enrollment distribution given an initial set of product attributes 505. As part of designing an adaptive conjoint analysis (ACA) questionnaire, one leverages consumer marketing database or demographic database from the U.S. Census Bureau so that the questionnaire can be tailored to each consumer 507, 509.

The fundamental idea is to iterate the process of adjusting product attributes, estimating product enrollment distributions, and calculating economic parameters (projected profit/loss as well as the level of subsidization inherent in a medical insurance product) of each product bundle so that we achieve an acceptable trade off between social insurance and moral hazard. That is, while the young and healthy are supposed to subsidize the cost of insurance for the old and sick, there needs to be an element of personal responsibility in benefit design so that people with poor health habits and beneficiary mentality do not abuse the entire healthcare system to the detriment of all 511, 513. In short, benefit design must deal effectively with risk factors that can be mitigated within socially acceptable means. The plot labeled 517 shows the relationship between individual prediction accuracy measured in R-sq or $R^2$ and group prediction accuracy measured in predictive ratio (PR) mean ($\mu$) and standard deviation (a). Individual predictive accuracy becomes less important as group size increases as in employer or group underwriting. However, in clinical settings and predicting benefit enrollment, where adverse selection can occur frequently, individual predictive accuracy is of paramount importance.

In healthcare, benefit design, according to prior art, is typically carried out by linking historical utilization and cost data to various benefit parameters, such as co-pay, deductible, co-insurance, maximum out-of-pocket, limits on Health Savings Account/Flexible Spending Account (HSA/FSA), etc. Then a loading factor (margin) is computed for each plan design, which sets the premium for the plan. Depending on the premium differential between plans, subsidization factors are calculated such that a plan attractive to predominantly the healthy (high-deductible plans) may subsidize the cost of another plan that appeals primarily to the sick so that the concept of social insurance can be preserved in plan design.

An important consideration in benefit design is risk management. If benefit parameters are particularly attractive to a certain segment of population whose medical needs differ significantly from those of the general population, then such a plan has a high likelihood of attracting a biased population, which can lead to unexpected profit or loss depending on the direction of the bias. Unfortunately for health insurance companies, this phenomenon of biased population (called anti- or adverse selection) is not uncommon. The result is a cookie-cutter benefit design with a small number of selections so that the law of large numbers dominates the field.

More recently under the banner of consumer-directed health plan (CDHP), many payers started introducing high-deductible, low-premium plans. The theory of the case for CDHP is that high-deductible plans with some form of medical savings account will turn beneficiary-mentality patients into sophisticated healthcare consumers. Unlike other consumer industries, healthcare consumers may have hard time correlating actual high-quality care with a perceived one of at least based on RAND's quality metrics. Furthermore, the initial thrust of CDHP was to attract the cream-of-the-crop population from employers offering plans from multiple payers. That is, nimble new-to-the-market payers introduced CDHP products to employers desperate to cut soaring health benefit costs. The end result was that dinosaur payers were saddled with the undesirable segment of the population, hurting their bottom line.

Studies suggest that while the young and healthy are potential winners of CDHP, their opportunities for savings are limited because of restrictions in plan design, such as portability and investment. Results of post-CDHP health-resource utilizations and costs suggest mixed results with no clear trend. Perhaps mixed results are not surprising given the ambiguity of the theory of the case.

Perhaps the biggest shortcoming of the current health plan design is that few incorporate innovative design parameters, such as consumer-engagement strategies, incentives for lifestyle changes, and fun aspects in linking validated evidence-based-medicine guidelines, nutrition and exercise to health. Our design approach leverages the estimation of a consumer-preference function and projected utility functions derived from the impact analysis engine to move away from a cookie-cutter design and towards a tailored plan design that impacts health behavior change.

For new product launch 501, one first proceeds with adaptive conjoint questionnaire (ACQ) 503 that is designed to minimize the number of questions leveraging predictive questionnaire construction. From ACQ responses, one can estimate a consumer preference function at an individual level. From a pool of initial product bundles with preset features, one estimates the overall enrollment distribution for a group (i.e., an employer). From the overall enrollment distribution and the outputs of multimode health-trajectory predictors, one computes profit/loss for each product and generate a three-dimensional picture of profit/loss and compressed two-dimensional objectives (i.e., minimize premium and out-of-pocket or OOP expense) as shown in relationships 515 and 517. This picture will provide visual insights to facilitate the understanding of Pareto-efficient design parameters, which can lead to the reconfiguration of product features. This process of enrollment prediction and product reconfiguration is iterative until the incremental change in product-feature reconfiguration is below an acceptable threshold.

After the product launch, one starts with a fresh data set, which represents the actual product selection behavior by consumers. Unlike in conjoint analysis, one does not have information on exactly which products consumers traded off before making product-selection decisions. One has the following information on consumers and their product-selection behavior:

1. Demographics and behavior marketing ($x_{demo}$, $x_{cbm}$)
2. Prior product selection ($x_{pps}$), which doesn't exist for new consumers
3. Current product selection The task at hand is to estimate a revised consumer preference function using real data. Let y and w denote the product-selection behavior and product features, respectively. Then, the estimation task is as follows:

$$\hat{y}=f(x_{demo},x_{cbm},x_{pps},w,D(w,y)),$$

where $D(w,y)$ is a distance function between w and y, and $f(\cdot)$ can be estimated using parametric or nonparametric learning algorithms. Any differences between the conjoint and real-data models are stored in a database for continuous model adaptation and learning. More complex design with incentives requires utility fanctions associated with incentives from the impact-analysis engine. After estimating the consumer-preference function, there is a secondary step of identifying intervention opportunities given the characteristics of consumers choosing each product bundle. Based on utility functions and the outputs of the multimode health-trajectory predictors, the remaining task is to design an incentive program within each product bundle that will encourage high-risk members to participate in the program.

Figure 6:
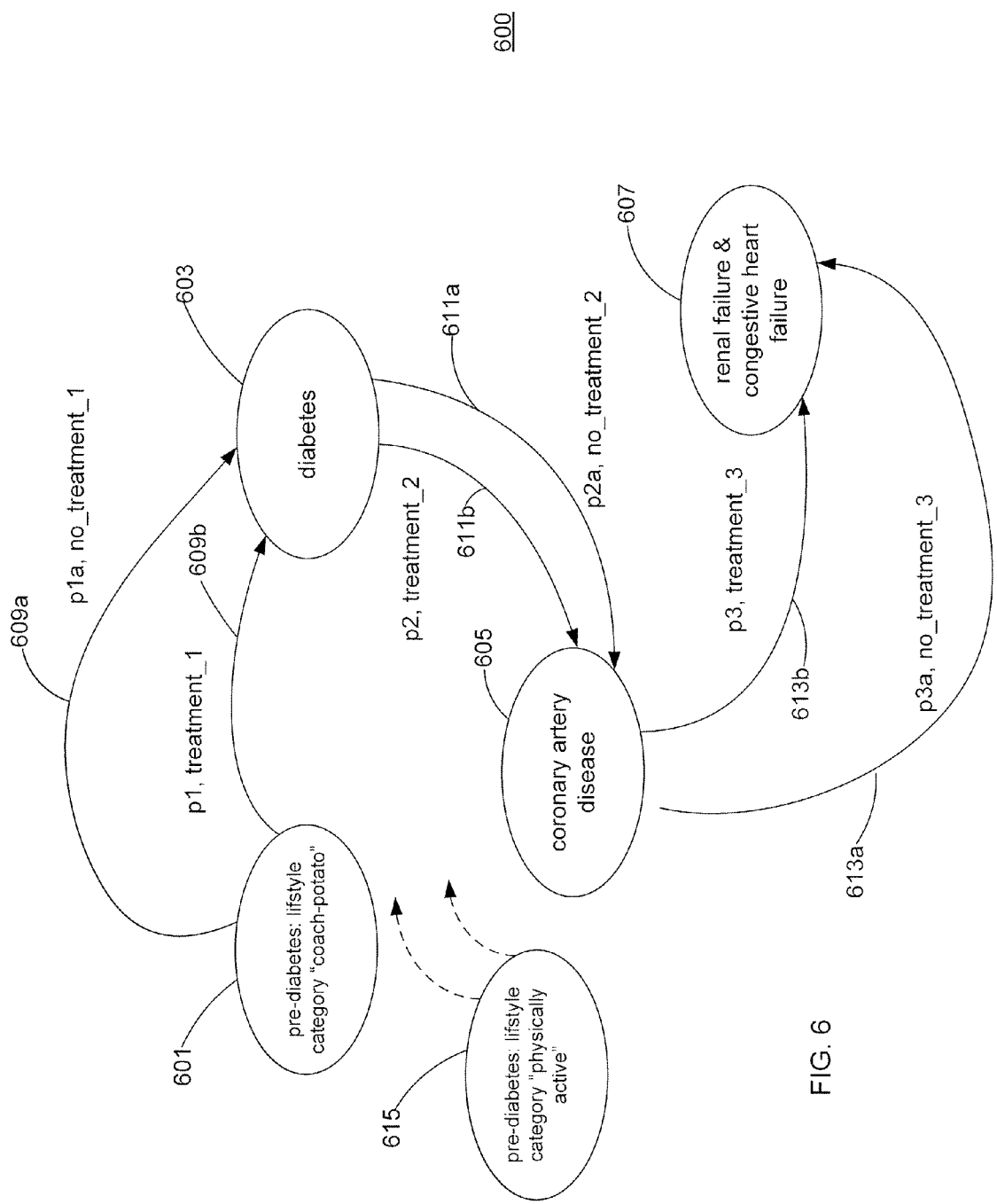
FIG. 6 shows an example of Markov modeling of assessing a target of opportunity in accordance with an embodiment of the invention.

FIG. 6 shows an example of Markov modeling of assessing a target of opportunity in accordance with an embodiment of the invention. Markov model 600 shows a disease progression related to diabetes. Markov model 600 shows the probability of transitioning from one disease state to another disease state based on whether the consumer obtains a prescribed treatment. Additionally, disease states may depend on observed behavioral/lifestyle factors including the attributes of the consumer. Attributes may include the category of life style (e.g., "coach-potato") and level of education of the consumer. The type of treatment and the efficacy of the treatment may depend on the consumer's attributes.

With state 601, a consumer, who is a "couch-potato," is determined to be a pre-diabetic. As determined by intervention opportunity finder 103 (as shown in FIG. 1), there is a probability $p_{1_a}$ 609a of the consumer becoming a diabetic (state 603) without any treatment and a probability $p_1$ 609b if the consumer received a prescribed treatment (treatment_1). For example, EBM supercharger 300 may determine that the consumer can substantially reduce the probability of becoming a diabetic with a proper diet and exercise regime under the supervision of a dietician and/or exercise coach.

When the consumer becomes a diabetic, there is a probability of developing coronary artery disease (corresponding to state 605). The corresponding treatment_2 (as determined by EBM supercharger) may be more radical than treatments. For example, treament_1 may include one or more prescribed drugs that are typically more costly than providing a dietician and/or exercise coach. (In general, as a disease progresses, the associated costs increase.) The probability of a diabetic developing coronary arterial disease without treatment is $p_{2_a}$ 611a and $p_2$ 611b with treatment.

In accordance with Markov model 600, once a consumer has developed coronary arterial disease, the consumer may further develop renal failure and/or congestive heart failure (state 607). The probability of developing renal failure/congestive failure is $p_{3_a}$ 113a without treatment is and $p_3$ 611b with treatment.

Markov model 600 may include states based on different attributes of a consumer. For example, state 615 is associated with the consumer having a physically active life style. Consequently, the transition probability of disease progression is typically smaller than a consumer having has a sedentary lifestyle (corresponding to state 601, in which a consumer is classified as a "coach-potato).

Exemplary Scenario

Sarah is a 45-year-old mother of two children, overweight, pre-diabetic, being treated for hypertension and hyperlipidemia. At work, she needs to enroll in a health benefit plan since her employer switched to a new payer, Global Health. In accordance with an embodiment of the invention, the following scenario that a consumer experiences.

Enrollment: Sarah is first given a combination of Predictive Health Risk Assessment (PHRA) interspersed with Adaptive Conjoint Analysis (ACA) questions. Even without single claims, PHRA calculates future health trajectories and guides Sarah through the benefit selection process based on an adaptive questionnaire tree designed to minimize the number of questions while maximizing predictive accuracy. She ends up selecting an HMO plan with various incentives for staying healthy. Impact analysis engine provided ROI's associated with incentives for consumers who fit Sarah's profile. She is given an instant analysis of her current health, likely health trajectories, and what she can do to prevent unpleasant outcomes. An interactive goal setting wraps up her first-day consumer experience with GH. Health trajectory predictors are based on PHRA/ACA questions, in which the optimal benefit design is part of resource allocation management (RAM). (With prior art, Sarah is typically given a list of traditional HMO, PPO, and Indemnity plans with a limited number of choices in deductibles, co-pays, and premium with health savings accounts.)

At-risk member identification: By virtue of PHRA, Sarah has already been identified as an at-risk member who can benefit from intervention. PHRA lists diabetes as a major risk factor given her current conditions, BMI, and lifestyle parameters inferred from external consumer behavior data obtained from Experian for a specific purpose of improving health guidance, not premium setting. Given her status, she gets a VAT call tailored to her situation, along with a two-page feedback/action plan letter based on her responses to the PHRA questionnaire all during the first week as part of a welcoming package. The Integrated Health Management Platform supports this function with health trajectory predictors, intervention opportunity finder; and RAM. (With prior art, since Sarah is a new member, GH must wait for claims data to accumulate before running a predictive model that predicts 12-month future cost. Because of claims lag, the typical wait time is 6 months.)

Maintenance: Based on earlier communications, Sarah understands what to do. She takes PHRA frequently to report her progress and to see if her health scores are improving. Upon meeting her first goal of losing 10 lbs in 4 weeks and improving her health scores by 10%, GH sends her a USB pedometer. Now she uses it to keep track of her activity level daily, uploading to her personal Web portal at GH activity data, which provides additional data points to the IHM Platform in order to improve guidance for Sarah. Meanwhile the IHM Platform is exploring healthcare database autonomously, looking for patterns that precede low-to-high or high-to-low transitions so that it can update its knowledge database. Furthermore, it is constantly monitoring the relationship between intervention and outcomes to ensure that every member gets the best possible touch points to maximize population health using both high-tech and human interventions. The multimode health-trajectory predictors perform predictions both on a regular basis and asynchronously (event-driven). All IHM components work seamlessly to make this happen. (With prior art, not knowing the full extent of her risk factors, she may live her life as she normally does. One day, she feels chest pain and goes to ER. Upon examination, they find out that she needs heart bypass. Further blood test shows her blood glucose level at 175 mg/dl, which makes her a diabetic, further complicating her recovery. About 3 months after her bypass surgery, GH finally has her claims data in an electronic data warehouse. The indigenous PM now flags her as a high-risk member—a clear case of regression to the mean and fixing the door after a cow has already left. A nurse calls her to inquire if anything can be done to help her.)

Computer Implementation

Figure 7:
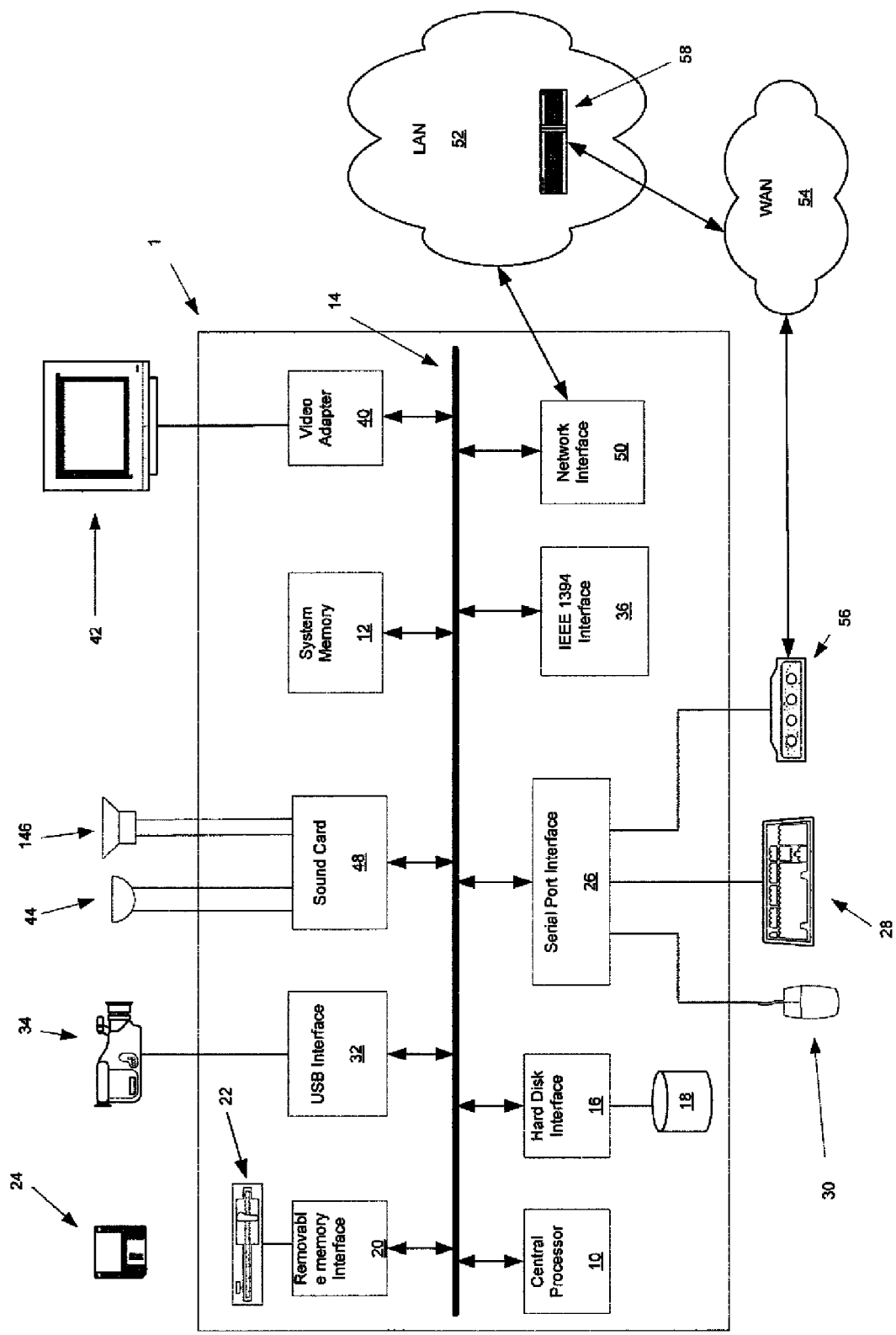
FIG. 7 shows computer system 100 that supports an embodiment of the invention.

FIG. 7 shows computer system 1 that supports an integrated health management platform (e.g., IHM platform 100 as shown in FIG. 1) in accordance with an embodiment of the invention. Elements of the present invention may be implemented with computer systems, such as the system 1. Computer system 1 includes a central processor 10, a system memory 12 and a system bus 14 that couples various system components including the system memory 12 to the central processor unit 10. System bus 14 may be any of several types of bus structures including a memory bus or memory controller, a peripheral bus, and a local bus using any of a variety of bus architectures. The structure of system memory 12 is well known to those skilled in the art and may include a basic input/output system (BIOS) stored in a read only memory (ROM) and one or more program modules such as operating systems, application programs and program data stored in random access memory (RAM).

Computer 1 may also include a variety of interface units and drives for reading and writing data. In particular, computer 1 includes a hard disk interface 16 and a removable memory interface 20 respectively coupling a hard disk drive 18 and a removable memory drive 22 to system bus 14. Examples of removable memory drives include magnetic disk drives and optical disk drives. The drives and their associated computer-readable media, such as a floppy disk 24 provide nonvolatile storage of computer readable instructions, data structures, program modules and other data for computer 1. A single hard disk drive 18 and a single removable memory drive 22 are shown for illustration purposes only and with the understanding that computer 1 may include several of such drives. Furthermore, computer 1 may include drives for interfacing with other types of computer readable media.

A user can interact with computer 1 with a variety of input devices. FIG. 7 shows a serial port interface 26 coupling a keyboard 28 and a pointing device 30 to system bus 14. Pointing device 28 may be implemented with a mouse, track ball, pen device, or similar device. Of course one or more other input devices (not shown) such as a joystick, game pad, satellite dish, scanner, touch sensitive screen or the like may be connected to computer 1.

Computer 1 may include additional interfaces for connecting devices to system bus 14. FIG. 7 shows a universal serial bus (USB) interface 32 coupling a video or digital camera 34 to system bus 14. An IEEE 1394 interface 36 may be used to couple additional devices to computer 1. Furthermore, interface 36 may configured to operate with particular manufacture interfaces such as FireWire developed by Apple Computer and i.Link developed by Sony. Input devices may also be coupled to system bus 114 through a parallel port, a game port, a PCI board or any other interface used to couple and input device to a computer.

Computer 1 also includes a video adapter 40 coupling a display device 42 to system bus 14. Display device 42 may include a cathode ray tube (CRT), liquid crystal display (LCD), field emission display (FED), plasma display or any other device that produces an image that is viewable by the user. Additional output devices, such as a printing device (not shown), may be connected to computer 1.

Sound can be recorded and reproduced with a microphone 44 and a speaker 66. A sound card 48 may be used to couple microphone 44 and speaker 46 to system bus 14. One skilled in the art will appreciate that the device connections shown in FIG. 7 are for illustration purposes only and that several of the peripheral devices could be coupled to system bus 14 via alternative interfaces. For example, video camera 34 could be connected to IEEE 1394 interface 36 and pointing device 30 could be connected to USB interface 32.

Computer 1 can operate in a networked environment using logical connections to one or more remote computers or other devices, such as a server, a router, a network personal computer, a peer device or other common network node, a wireless telephone or wireless personal digital assistant. Computer 1 includes a network interface 50 that couples system bus 14 to a local area network (LAN) 52. Networking environments are commonplace in offices, enterprise-wide computer networks and home computer systems.

A wide area network (WAN) 54, such as the Internet, can also be accessed by computer 1. FIG. 7 shows a modem unit 56 connected to serial port interface 26 and to WAN 54. Modem unit 56 may be located within or external to computer 1 and may be any type of conventional modem such as a cable modem or a satellite modem. LAN 52 may also be used to connect to WAN 54. FIG. 7 shows a router 58 that may connect LAN 52 to WAN 54 in a conventional manner.

It will be appreciated that the network connections shown are exemplary and other ways of establishing a communications link between the computers can be used. The existence of any of various well-known protocols, such as TCP/IP, Frame Relay, Ethernet, FTP, HTTP and the like, is presumed, and computer 1 can be operated in a client-server configuration to permit a user to retrieve web pages from a web-based server. Furthermore, any of various conventional web browsers can be used to display and manipulate data on web pages.

The operation of computer 1 can be controlled by a variety of different program modules. Examples of program modules are routines, programs, objects, components, and data structures that perform particular tasks or implement particular abstract data types. The present invention may also be practiced with other computer system configurations, including hand-held devices, multiprocessor systems, microprocessor-based or programmable consumer electronics, network PCS, minicomputers, mainframe computers, personal digital assistants and the like. Furthermore, the invention may also be practiced in distributed computing environments where tasks are performed by remote processing devices that are linked through a communications network. In a distributed computing environment, program modules may be located in both local and remote memory storage devices.

In an embodiment of the invention, central processor unit 10 determines health trajectory predictors from HRA data 151, claims data 153, and CBM data 155 (as shown in FIG. 1), which are obtained through LAN 152 and WAN 154. Central processor unit 10 may also provide the functionalities of intervention opportunity finder 103, resource allocation manager 105, and impact analysis engine 107. Consequently, central processor unit 10 may provide a target of opportunity for a consumer from evidence-based medicine (EBM) guidelines or medical journals 351 (as shown in figure 35). EBM guidelines (corresponding to EBM database 317) and electronic health records (EHR) (corresponding to EHR database 203) may be retrieved from hard disk drive 18.

As can be appreciated by one skilled in the art, a computer system with an associated computer-readable medium containing instructions for controlling the computer system may be utilized to implement the exemplary embodiments that are disclosed herein. The computer system may include at least one computer such as a microprocessor, a cluster of microprocessors, a mainframe, and networked workstations.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

I claim:

1. A method for managing healthcare, comprising:

obtaining multi-dimensional input data for each of a plurality of consumers, the multi-dimensional data including, for each consumer, claim data, self-reported data, and consumer behavior marketing data for the consumer, the consumer behavior marketing data further including behavior, lifestyle, and attitudinal information about the consumer;

a computer using the multi-dimensional input data to iteratively generate a set of clusters for each of a plurality of outcome variables, wherein the clusters for each outcome variable are generated to maximize an output dispersion compression by comparing a ratio of a dispersion of each cluster and an overall dispersion of a population to a predetermined dispersion-compression threshold;

a computer assigning a first consumer to at least one cluster according to multi-dimensional input data for the consumer;

a computer determining for the first consumer at least one health-trajectory prediction from a model associated with the at least one cluster for the first consumer and the multi-dimensional input data for the first consumer;

the computer identifying a target of opportunity for the consumer in accordance with the at least one health-trajectory prediction; and the computer offering the target of opportunity for the first consumer.

2. The method of claim 1, further comprising:
inferring a characteristic of the first consumer from a subset of the multidimensional input data for the first consumer.

3. The method of claim 1, further comprising:
associating a disease progression based on one of the at least one cluster, said one of the at least one cluster being associated with at least one attribute of the consumer.

4. The method of claim 3, wherein the target of opportunity is determined from said one of the at least one cluster and the disease progression.

5. The method of claim 4, further comprising:
assessing an impact of the target of opportunity for the first consumer.

6. The method of claim 5, wherein assessing the impact of the target of opportunity comprises using a Markov model.

7. The method of claim 1, further comprising:
extracting the target of opportunity from medical information using a set of rules for the multi-dimensional input data for the first consumer.

8. The method of claim 1, the multi-dimensional input data further including health risk assessment data.

9. The method of claim 1, the multi-dimensional input data further including biometric data.

10. The method of claim 1, further comprising:
forming a consensus view when the consumer belongs to a plurality of clusters.

11. The method of claim 1, further comprising:
identifying a previous event that occurred to a subsequent transition event; and
measuring a correlation between the previous event and the subsequent transition event.

12. The method of claim 1, further comprising:
sending a reminder to the consumer if the consumer does not utilize the target of opportunity, wherein the target of opportunity for the consumer is in accordance with the at least one health-trajectory prediction.

13. The method of claim 1, the assigning comprising:
determining a lifestyle of the consumer; and
combining a health condition of the consumer with the lifestyle for assigning the consumer to said one of the at least one cluster.

14. The method of claim 1, further comprising:
determining at least one unobserved trait of the first consumer from the multidimensional input data; and
tailoring an intervention strategy for the first consumer from the at least one unobserved trait.

15. An apparatus that manages healthcare, comprising:
a memory; and
a processor accessing the memory to obtain computer-executable instructions, and the processor executing the computer-executable instructions to perform the following operations:
obtaining multi-dimensional input data for each of a plurality of consumers, the multi-dimensional data including, for each consumer, claim data and consumer behavior marketing data for the consumer;
using the multi-dimensional input data to iteratively generate a set of clusters for each of a plurality of outcome variables, wherein the clusters for each outcome variable are generated to maximize an output dispersion compression by comparing a ratio of a dispersion of each cluster and an overall dispersion of a population to a predetermined dispersion-compression threshold;
assigning a first consumer to at least one cluster according to multi-dimensional input data for the consumer;
determining, for the first consumer, at least one health-trajectory predictor from a model associated with the at least one cluster for the first consumer and the multi-dimensional input data for the first consumer;
identifying a target of opportunity for the consumer in accordance with the at least one health-trajectory predictor; and
offering the target of opportunity to the consumer.

16. The apparatus of claim 15, the processor further executing the computer-executable instructions for performing the following operation:
forming a consensus view when the consumer is assigned to a plurality of clusters.

17. The apparatus of claim 16, the processor further executing the computer-executable instructions for performing the following operations:
associating a disease progression based on one of the at least one cluster, said one of the at least one cluster being associated with at least one attribute of the consumer, wherein the target of opportunity is determined from said one of the at least one cluster and the disease progression.

18. The apparatus of claim 17, the processor further executing the computer-executable instructions for performing the following operation:
assessing an impact of the target of opportunity for the first consumer.

19. A non-transitory computer-readable medium having computer-executable instructions that, when executed by a computer, cause the computer to perform operations comprising:
obtaining multi-dimensional input data for each of a plurality of consumers, the multi-dimensional data including, for each consumer, claim data and consumer behavior marketing data for the consumer;

a computer using the multi-dimensional input data to iteratively generate a set of clusters for each of a plurality of outcome variables, wherein the clusters for each outcome variable are generated to maximize an output dispersion compression by comparing a ratio of a dispersion of each cluster and an overall dispersion of a population to a predetermined dispersion-compression threshold;

a computer assigning a first consumer to at least one cluster according to multi-dimensional input data for the consumer;

determining, for the first consumer, at least one health-trajectory predictor from a model associated with the at least one cluster for the first consumer and the multi-dimensional input data for the first consumer;

identifying a target of opportunity for the consumer in accordance with the at least one health-trajectory predictor; and offering the target of opportunity to the first consumer.

20. The non-transitory computer-readable medium of claim 19, wherein the instructions further cause the computer to perform operations comprising:

assigning the first consumer to another cluster based on the multi-dimensional input data; and forming a consensus view when the first consumer belongs to a plurality of clusters.

21. A computer-implemented method, comprising:

obtaining multi-dimensional input data for a consumer, the multi-dimensional input data including claim data, self-reported data, and consumer behavior marketing data;

using the multi-dimensional input data to iteratively generate a set of clusters for each of a plurality of outcome variables, wherein the clusters for each outcome variable are generated to maximize an output dispersion compression by comparing a ratio of a dispersion of each cluster and an overall dispersion of a population to a predetermined dispersion-compression threshold;

assigning the consumer to a particular cluster in the set of clusters, wherein the clusters are defined according to an impact of treatment on consumers in each cluster;

determining a health trajectory prediction for the consumer according to the multi-dimensional input data and a model specific to the particular cluster, wherein the health trajectory prediction predicts a future status of a health of the consumer according to disease progression, engagement, and impact;

identifying a target of opportunity from the health trajectory prediction, wherein the target of opportunity comprises a treatment for a disease of the consumer; and presenting the target of opportunity to the consumer;

wherein the obtaining, using, assigning, determining, identifying, and presenting are performed by one or more computers.

22. The method of claim 21, further comprising generating the set of clusters to maximize an output dispersion compression for the plurality of clusters.

23. The method of claim 21, further comprising determining at least one unobserved trait of the consumer from the multidimensional input data.

24. The method of claim 21, further comprising using a Markov model to estimate an impact of the target of opportunity on the consumer.

* * * * *